United States Patent [19]
Schmitt

[11] Patent Number: 5,647,743
[45] Date of Patent: Jul. 15, 1997

[54] DEVICE FOR TREATING JAW FRACTURES OR TOOTH DISPLACEMENTS

[76] Inventor: Friedrich Schmitt, Katharienenufer 12, D-54290 Trier, Germany

[21] Appl. No.: 454,280

[22] PCT Filed: May 11, 1994

[86] PCT No.: PCT/EP94/01528

§ 371 Date: Jun. 16, 1995

§ 102(e) Date: Jun. 16, 1995

[87] PCT Pub. No.: WO94/26197

PCT Pub. Date: Nov. 24, 1994

[30] Foreign Application Priority Data

May 11, 1993 [DE] Germany .................... 43 15 585.5
May 11, 1993 [DE] Germany .................... 9307108 U

[51] Int. Cl.⁶ ........................................... A61C 7/00
[52] U.S. Cl. .................................... 433/23; 433/22
[58] Field of Search ............................. 433/23, 22

[56] References Cited

U.S. PATENT DOCUMENTS

| 1,114,624 | 10/1914 | Meier | 433/12 |
| 1,292,885 | 1/1919 | Rodgers | 433/12 |
| 4,840,562 | 6/1989 | Wilson et al. | 433/23 |
| 4,856,992 | 8/1989 | Bergersen | 433/18 |
| 5,257,439 | 11/1993 | LeBlanc | 24/269 |

FOREIGN PATENT DOCUMENTS

| B 10 29 981 | 5/1958 | Germany | 433/23 |
| 3915807 | 11/1990 | Germany . | |
| 4119942 | 1/1993 | Germany . | |

OTHER PUBLICATIONS

Von Dr. Harald Schienbein, "Konstruktionsprinzipien Kieferorthopädische Schrauben," dental–labor, Jun., 1972, pp. 27–30.

Primary Examiner—Edgar S. Burr
Assistant Examiner—Dave A. Ghatt
Attorney, Agent, or Firm—Speckman, Pauley & Fejer

[57] ABSTRACT

A device for the orthopedic treatment of jaw fractures or tooth displacements has ring-shaped dental bands which surround the teeth and are detachably secured to at least two teeth of a jaw. In order to attach the dental band to the tooth in a secure and detachable manner, at least two tensioning blocks are integrally shaped on the dental band. The tensioning blocks are arranged in pairs at a distance from each other, aligned bores and/or threaded holes are created in both tensioning blocks and the gap may be reduced by means of at least one tensioning screw held in the bores or threaded holes.

20 Claims, 5 Drawing Sheets

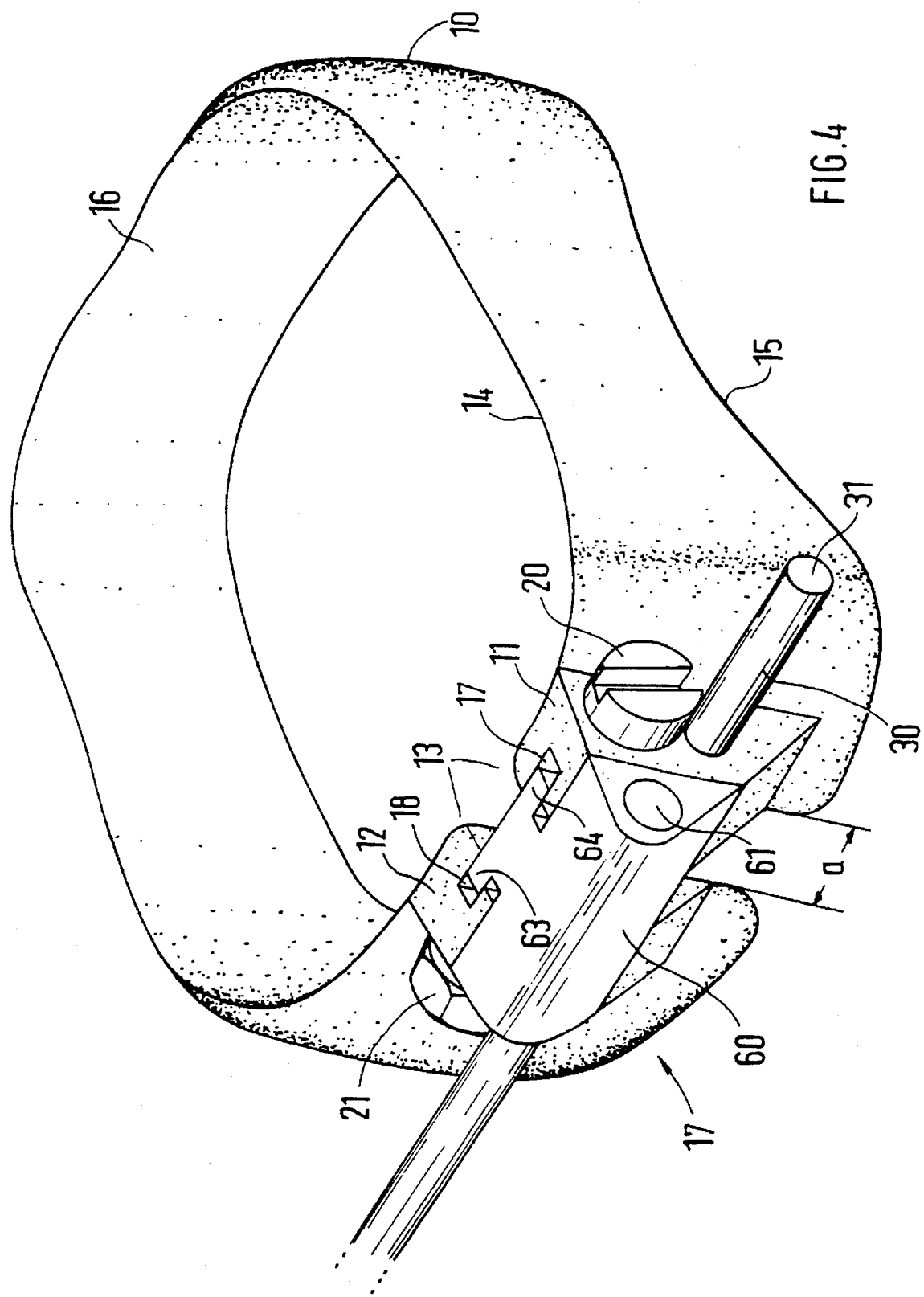

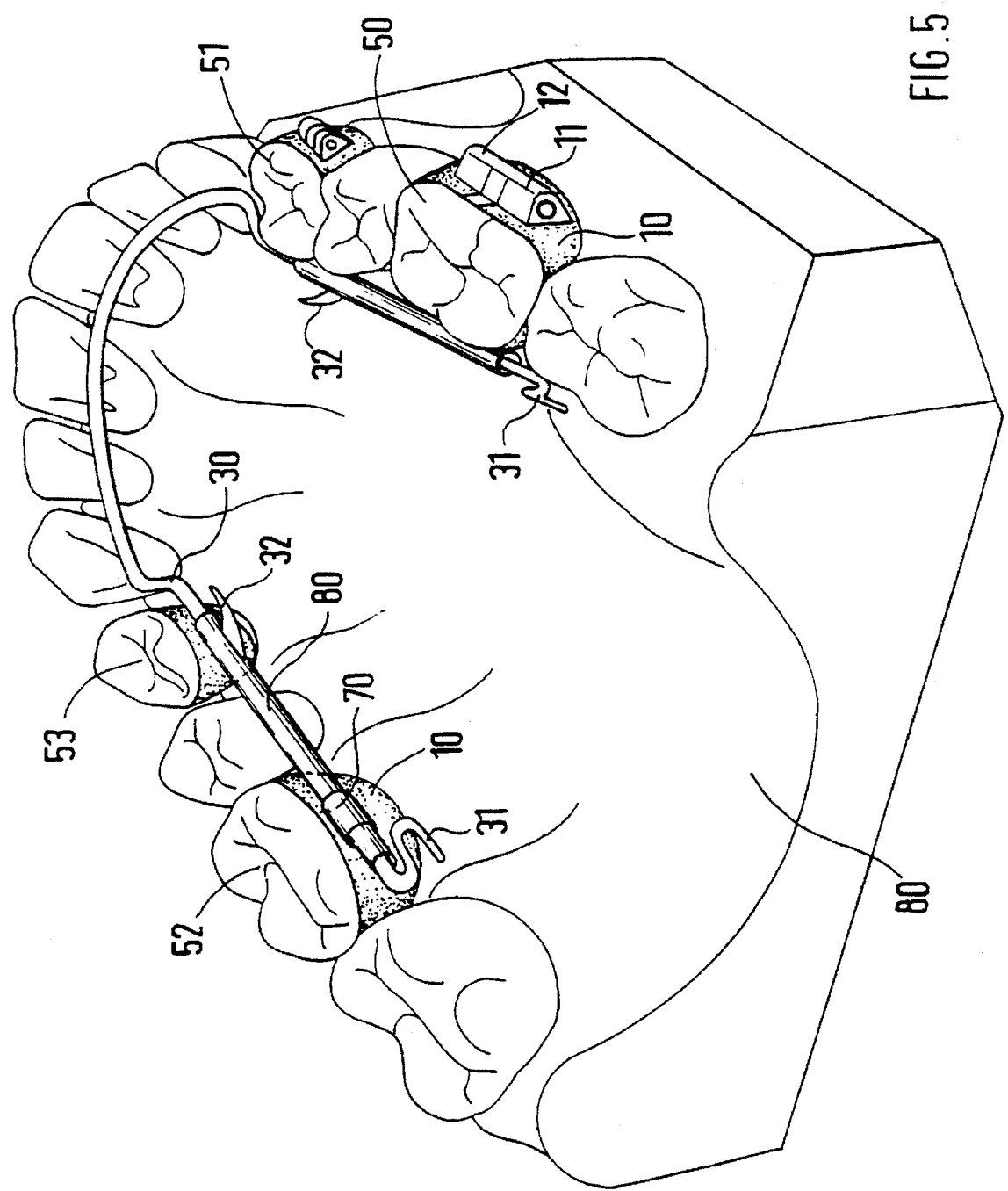

DEVICE FOR TREATING JAW FRACTURES OR TOOTH DISPLACEMENTS

BACKGROUND OF THE INVENTION

1. Field of the Invention

This invention relates to a device for orthopedic treatment of jaw fractures or misaligned teeth, wherein ring-shaped dental bands which loop around the teeth are releasably fastened to at least two teeth of a jaw.

2. Description of Prior Art

Such appliances are commercially available in many varied embodiments. Ring-shaped dental bands are fastened by a special cement on individual teeth of a jaw. Short tubes are soldered to the dental bands and are used for receiving straps and tensioning elements. The tensioning elements transfer directed forces to the individual teeth and thus also to the jaw.

Food remnants enter the area between the dental band and the tooth during eating and are converted into aggressive acids, which after prolonged reaction attack and destroy the enamel of a tooth. Regular cleaning of the space is omitted because the cemented connection would have to be removed, which also causes damage to the tooth enamel.

Another device is known from DE 41 19 942 A1. In this case a strip of material is placed around the outer surface of a tooth. A holder is soldered to the one end of the strip of material, the other end is bent to form a loop-like receiver. A wire is threaded into the loop-shaped receiver and placed around the holder. The free ends of the wire are twisted together, so that the ends of the dental band move toward each other and thus clamp the dental band around the tooth.

Such a dental band can only be employed with those teeth which have a distance from neighboring teeth which is greater than the thickness of the dental band. However, with misaligned teeth in particular the teeth are placed closely together and the dental band cannot easily be placed around the tooth. A special hammer which is used for placing ring-shaped dental bands cannot be used here, since the strip of material has a relatively high degree of instability and tends to bend. A further disadvantage of such a device is that sufficient tensioning forces cannot be achieved because of the twisting of the wire ends, so that the dental band cannot absorb large reaction forces, such as those which occur in connection with correcting misaligned teeth. As a result, the conventional dental bands are displaced on the tooth and the transmitted forces act in uncontrollable directions. For compensation the dental band is provided with holes which can be filled with a special cement, so that the dental band is also held by a connection between the materials. However, the known disadvantages for the tooth enamel again occur because of cementing.

SUMMARY OF THE INVENTION

It is one object of this invention to provide a device of the previously mentioned type which allows the simple secure fastening of a dental band on a tooth and which can be removed from the oral space and inserted again without damaging the tooth in the process.

The above object of this invention is accomplished with at least two tensioning blocks that are formed integrally on the dental band, wherein the tension blocks are arranged in pairs and have a distance from each other. Aligned bores and/or threaded receivers are cut in both tensioning blocks and the distance can be reduced by means of at least one tensioning screw maintained in the bores or threaded receivers.

A high degree of freedom from distortion is provided by a closed profile. Thus the dental band can be placed on a tooth with a special hammer even where teeth are placed extremely close to each other, without the dental band bending or buckling. Large forces can be exerted on the tensioning blocks with the threaded connection, so that the dental band grips the tooth securely and immovably. The tensioning screw can be easily released with a wrench and the appliance can therefore quickly and easily be taken out of the oral space and put back again. The teeth can then be cleaned and treated with fluoride, for example.

According to one preferred embodiment of this invention, the bores are cut in the tensioning blocks in such a way that one tensioning screw is disposed in the area of an upper edge and a further tensioning screw in the area of a lower edge of the dental band. The dental band can be conformed in the upper and lower areas to the shape of the tooth by adjusting the two tensioning screws, so that custom adaptation to the dental geometry of each tooth is possible.

If tensioning blocks are disposed on sides of the dental band which are located opposite each other, it is possible to achieve an even distribution of the tensioning force. When the dental band is tightened, the two tensioning blocks move toward each other. This causes a relative movement between the side of the dental band facing the tooth and the tooth. To prevent damage to the tooth surface, it is advantageous to form rounded transitions at the transition areas where the dental band is not in contact with the tooth.

For the connection of two dental bands with each other and for being able to transfer directed force effects to the teeth, according to one preferred embodiment, bores are cut into tensioning blocks having central axes which are aligned with respect to each other, wherein wire-like straps can be introduced into the bores. In this connection a fastening option for the strap on the dental band is provided wherein one bore is embodied as a fitted bore for fixing the strap in place, into which the strap can be pressed with its free end. The strap can also be fixed in the bore by a connection between the materials, such as soldering or gluing.

A continuous adjustment possibility, which permits a force variation and a compensation of the displacement of the teeth, for example because of the correction of misaligned teeth, can be achieved in a simple manner. A threaded receiver is cut in the first tensioning block and, aligned therewith, a further threaded receiver in the second tensioning block. An exterior thread disposed on the free end of the strap can be introduced into the threaded receivers and a clamping nut can be screwed on the exterior thread in the space formed between the two tensioning blocks.

In another preferred embodiment according to this invention, a strap is provided on the dental band and a holder is disposed in the space formed between the two tensioning blocks. The holder has a bore into which the tensioning screw is introduced. The holder has receivers on its side facing away from the dental band for the passage and/or fastening of straps. In this connection it is advantageous for the holder to be releasably connected with one or with both tensioning blocks.

In another preferred embodiment according to this invention, the shoulders are formed on the holder which can be inserted into recesses of the tensioning blocks, wherein one of the shoulders is maintained by a connection between the materials or frictionally connected in one of the recesses. In this manner the holders can be quickly and simply mounted or replaced.

So that a force can be transferred to the outside of the tooth as well as the inside of the tooth, additional holders can be fastened on the side of the dental band facing away from the tooth and the holders can be used for fastening straps or pieces of tubes.

BRIEF DESCRIPTION OF THE DRAWINGS

This invention will be explained in more detail below by means of exemplary embodiments of the invention represented in the drawings wherein:

FIG. 4 is a perspective view of a dental band with a holder which can be pushed on; and FIG. 5 shows a placement of a device for correcting misaligned teeth as a plaster model of a jaw.

DESCRIPTION OF PREFERRED EMBODIMENTS

Figure 1:
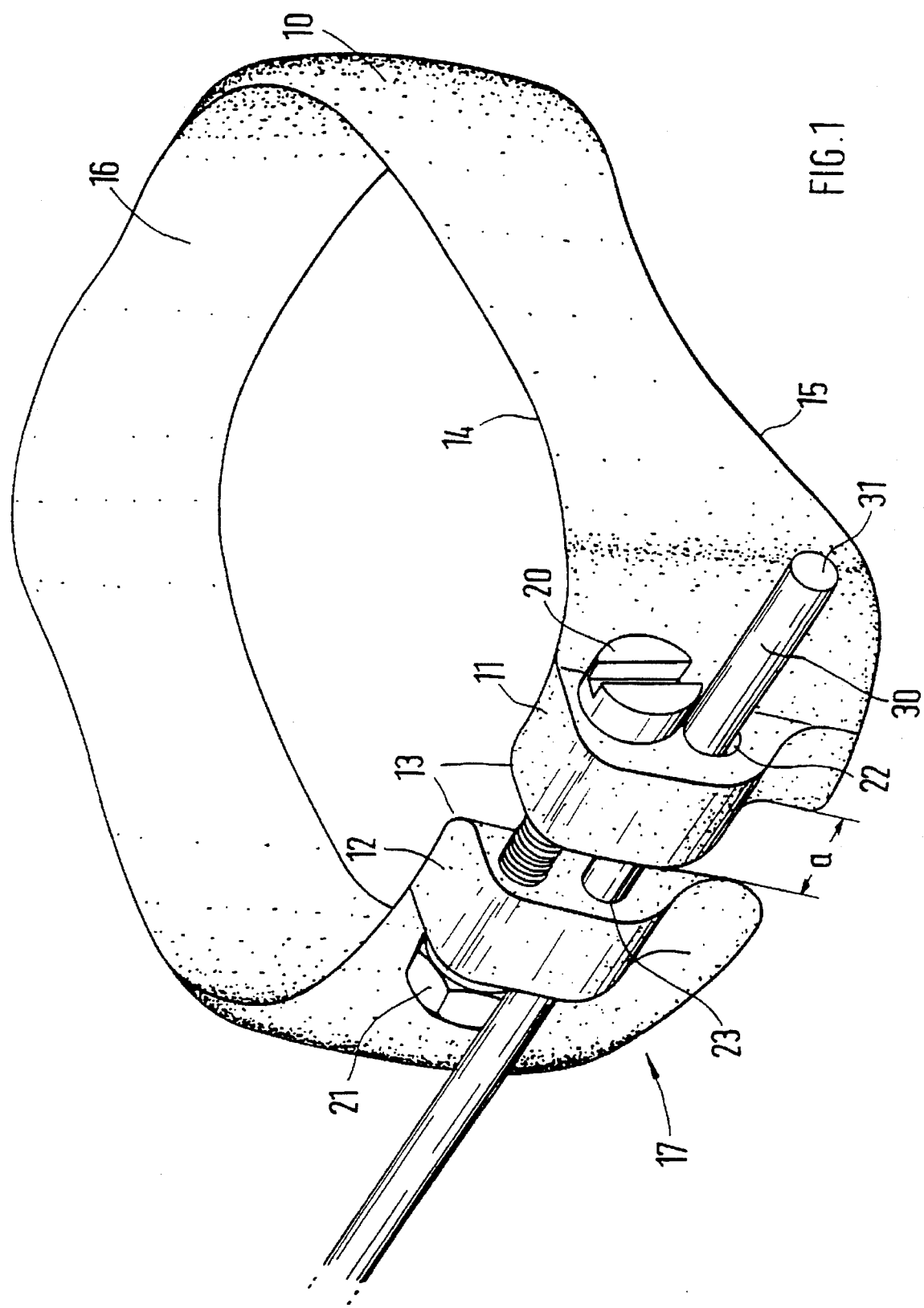
FIG. 1 is a perspective view of a dental band with a strap.

A dental band 10 is shown in FIG. 1, on which two tensioning blocks 11, 12 are integrally formed on a front 17 of the dental band 10. The dental band 10 is shown as ring-shaped and has a generally closed profile. Threaded receivers aligned with each other are cut into the tensioning blocks 11, 12, into which a tensioning screw is inserted and secured on the tensioning block 12 by means of a nut 21. Further aligned bores 22, 23 are cut into the tensioning blocks 11, 12. The bore 23 is embodied as a fitted bore. The strap 31 is inserted into the bore 22 and is held in the bore 23. It is also possible not to provide the bore 23 as a fitted bore. In that case the strap 31 is preferably soldered to the tensioning block 12 to achieve a fixed and immovable seat.

The dental band 10 can be pushed on the tooth with its lower edge 15. Since with teeth set close together the gap between two adjoining teeth is often less than the thickness of the dental band 10, forces are often exerted with the aid Of a special hammer on the upward facing sides of the tensioning blocks 11, 12 so that the dental band 10 is driven between the teeth.

A distance formed between the tensioning blocks 11, 12 can be reduced by means of a tensioning screw 20 once the dental band 10 is set on the tooth. A nut 21 receives the tensioning screw 20. The nut 21 is preferably fixed against relative rotation on the tensioning block 12 or, the nut 21 can be held by means of a wrench during the tensioning process.

Figure 2:
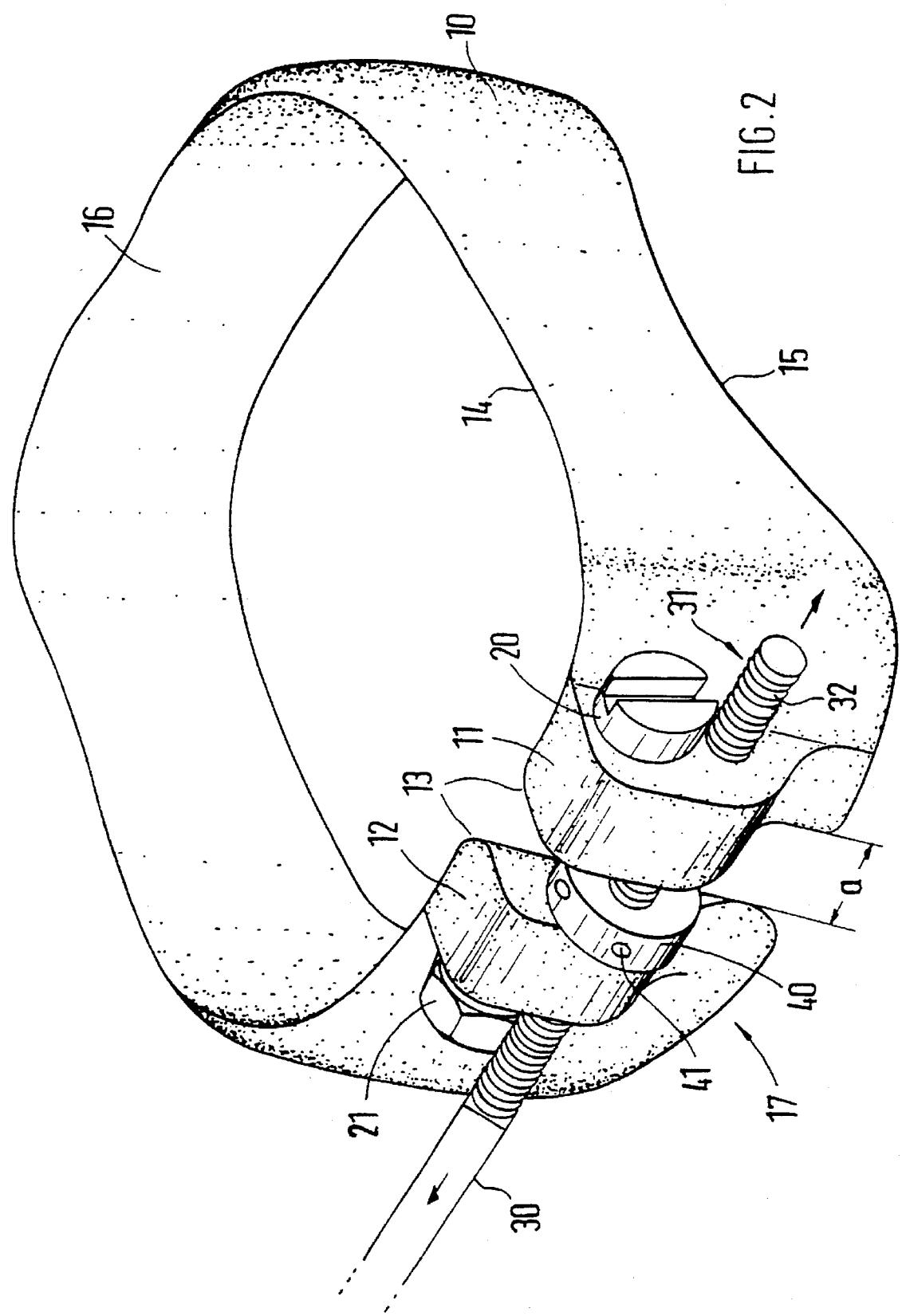
FIG. 2 is a perspective view of a dental band with a strap which can be adjusted in an axial direction.

A further preferred embodiment according to this invention is shown in FIG. 2. Aligned bores are cut into both tensioning blocks 11, 12, into which a strap 30 is inserted. The strap end is preferably embodied as a screw thread 32. A tensioning nut 40 is disposed between the two tensioning blocks 11, 12 and is engaged with the screw thread 32. Tool receivers 41 are disposed on the tensioning screw 40 by means of which the tensioning screw 40 can be rotated. In this way the strap 30 can be continuously displaced in the screw receivers of the tensioning blocks 11, 12. It is thus possible, for example, to firmly clamp two dental bands which are connected via the strap 30, or movements of the teeth because of the correction of their position in the jaw, for compensation.

Figure 3:
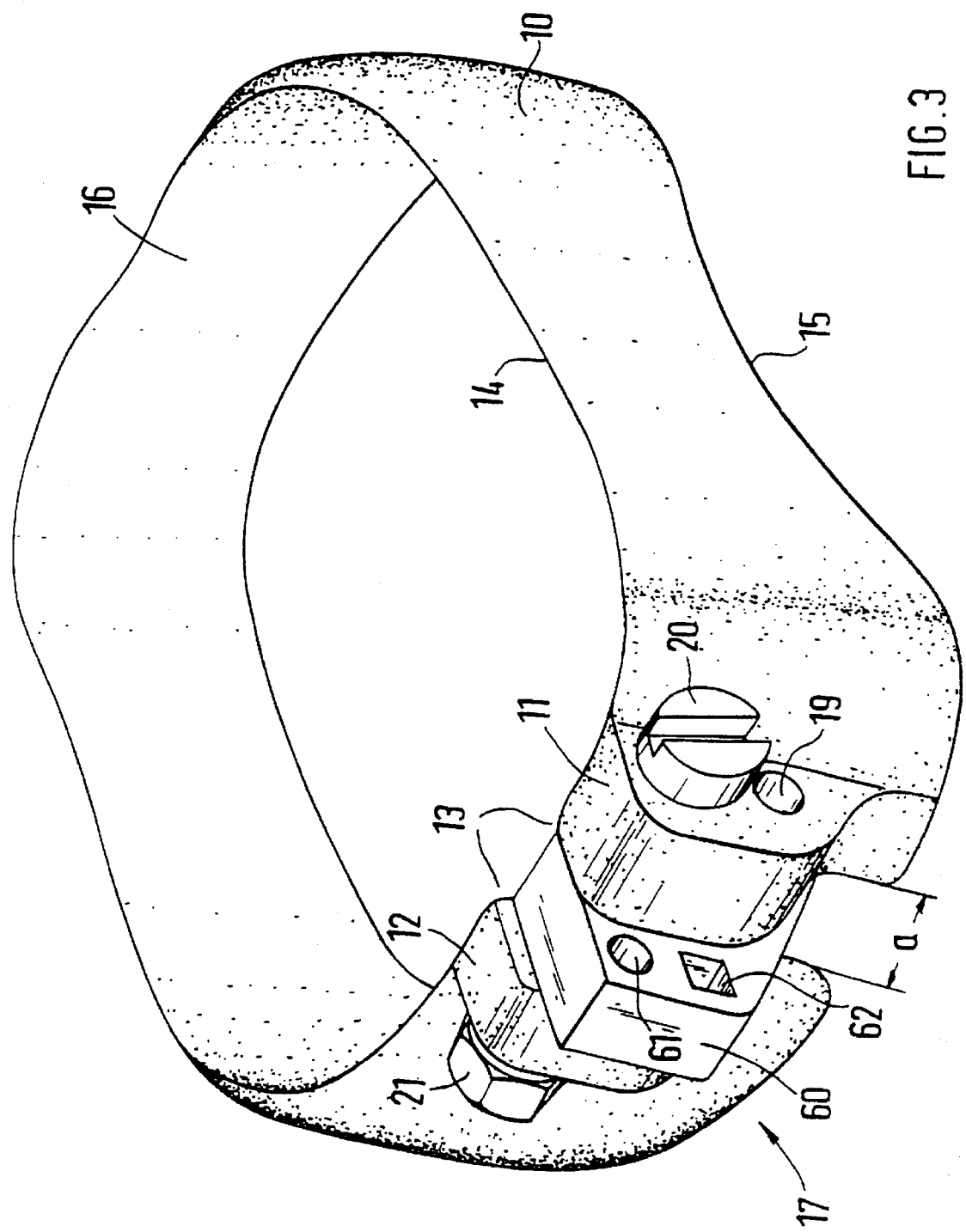
FIG. 3 is a perspective view of a dental band with a holder disposed between two tensioning blocks.

Additional preferred embodiments for fastening straps 30 on dental bands 10 are shown in FIGS. 3 and 4.

A holder 60 is disposed between the tensioning blocks 11, 12, as shown in FIG. 3. The holder 60 has two bores, by means of which the holder 60 can be fastened on the dental band 10. The tensioning screw 20 is inserted into the one bore, and into the other bore is a guide pin which can be fixed to the tensioning block 11 in a fitted receiver 19. The tensioning block 12 has a bore in which a guide pin is displaceably guided. Guidance is thus possible during tensioning when tightening the tensioning screw 20, and in addition a stiffening of the dental band 10 is possible. Two holes 61, 62 are cut in the holder and are used to receive straps 30. The straps 30 can be either displaceably seated in the holes or can be held by means of a fitted seating or a connection between the materials, such as soldering, or an adhesive connection.

A holder 60 having two guide shoulders 63, 64 is shown in FIG. 4. These guide shoulders 63, 64 are inserted in guide recesses 17, 18 of the tensioning blocks 11, 12. The guide shoulder 63 is held in the guide recess 18. However, the other guide shoulder 64 is displaceably seated in the guide recess 17. In this way the holder 60 can also be easily attached to the dental band 10 later, and the option of a tensioning process as well as that of releasing the dental band 10 from the tooth is preserved without hindrance.

A placement situation of a device for correcting misaligned teeth by means of a plaster model of a jaw is shown in FIG. 5. Respectively one dental band 10 is placed around the teeth 50, 51, 52 and 53 and is clamped to the teeth 50, 51, 52, and 53. Holders 70 are soldered on the dental bands 10. A section of a tube 80 is inserted into the holders 70 and soldered on, respectively on the left and right sides of the jaws. A curved strap 30 is inserted into the tubes 80, having ends which are bent to form hook-shaped tensioning band receivers 31. Further tensioning band receivers 32 are disposed on the side of the tube 80 facing away from the tensioning band receiver 31. Dental bands 10, such as rubber rings, not shown in FIG. 5, are fastened on these tensioning band receivers 32, 31 and transmit forces to the strap 30. Thus the strap 30 is pressed against the front row of teeth so that here a correction of misaligned teeth can be achieved.

I claim:

1. In a device for orthopedic treatment of jaw fractures or misaligned teeth, wherein a ring shaped dental band which loops around a tooth is releasably fastened to at least two teeth of a jaw, the improvement comprising:

at least two tensioning blocks (11, 12) formed integrally on the dental band (10), wherein the tensioning blocks (11, 12) are arranged in pairs and are at a distance from each other, each of the at least two tensioning blocks (11, 12) having at least one of aligned bores and aligned threaded receivers, at least one tensioning screw (20) engaged within the at least one of aligned bores and aligned threaded receivers, a holder (60) disposed in a space formed between the two tensioning blocks (11, 12), the holder (60) having a holder bore into which the tensioning screw (20) is engaged, and the holder (60) having a plurality of receivers (61, 62) on a side facing away from the dental band (10) for accommodating a strap (30).

2. In a device in accordance with claim 1, wherein the at least two tensioning blocks (11, 12) have the aligned bores (22, 23), the aligned bores (22, 23) are positioned in the at least two tensioning blocks (11, 12) such that one said tensioning screw (20) is disposed in an upper area near an upper edge (14) of the dental band (10) and another said tensioning screw (20) is disposed in a lower area near a lower edge (15) of the dental band (10).

3. In a device in accordance with claim 2, wherein the tensioning blocks (11, 12) are disposed on the dental band (10) and adjacent with respect to each other.

4. In a device in accordance with claim 3, wherein a rounded transition is formed at a transition area (13) where the dental band (10) is spaced from the tooth (50).

5. In a device in accordance with claim 4, wherein the aligned bores (22, 23) are positioned in the tensioning blocks (11, 12) with central axes of the aligned bores (22, 23) aligned with respect to each other, and a wire-like strap (30) is positioned within the bores (22, 23).

6. In a device in accordance with claim 5, wherein the strap has a free end (31) and said free end (31) is press-fitted within one of the aligned bores (22, 23).

7. In a device in accordance with claim 6, wherein the strap (30) is fixed in one of the aligned bores (22, 23) by an adhesive connection.

8. In a device in accordance with claim 1, wherein the at least two tensioning blocks (11, 12) have aligned threaded receivers, a strap (30) having a free end (31) with exterior threads (32) disposed on the free end (31) and engaged with internal threads of the threaded receivers, and a clamping nut (40) is engaged with the exterior threads (32) in a space formed between the two tensioning blocks (11, 12).

9. In a device in accordance with claim 8, wherein the holder (60) is releasably connected with at least one of the tensioning blocks (11, 12).

10. (Amended) In a device in accordance with claim 9, wherein
the at least two tensioning blocks (11, 12) each has a recess (17, 18), a plurality of shoulders (63, 64) are formed on the holder (60), and the shoulders (63, 64) are mounted within the recesses (17, 18) of the at least two tensioning blocks (11, 12).

11. In a device in accordance with claim 10, wherein a strap holder (70) is fastened on a side of the dental band (10) facing away from the tooth (50), and the strap holder (70) fastens the strap (30).

12. In a device in accordance with claim 10, wherein a strap holder (70) is fastened on a side of the dental band (10) facing away from the tooth (50), and a tube (80), the strap holder (70) fastens the tube (80).

13. In a device in accordance with claim 1, wherein the tensioning blocks (11, 12) are disposed on the dental band (10) and adjacent with respect to each other.

14. In a device in accordance with claim 1, wherein a rounded transition is formed at a transition area (13) where the dental band (10) is spaced from the tooth (50).

15. In a device in accordance with claim 1, wherein each of the at least two tensioning blocks (11, 12) have aligned bores (22, 23), the aligned bores (22, 23) are positioned in the tensioning blocks (11, 12) with central axes of the aligned bores (22, 23) aligned with respect to each other, and a wire-like strap (30) is positioned within the bores (22, 23).

16. In a device in accordance with claim 15, wherein one bore (22) of the aligned bores (22, 23) is shaped as a fitted bore for accommodating a free end (31) of the strap (30) and forming a pressed fit of the free end (31) within the one bore (22).

17. In a device in accordance with claim 1, wherein the tensioning blocks (11, 12) have aligned bores (22, 23), and a strap (30) is fixed in one of the aligned bores (22, 23) by an adhesive connection.

18. In a device in accordance with claim 1, wherein the holder (60) is releasably connected with at least one of the tensioning blocks (11, 12).

19. In a device in accordance with claim 1, wherein the at least two tensioning blocks (11, 12) each has a recess (17, 18), a plurality of shoulders (63, 64) are formed on the holder (60), and the shoulders (63, 64) are mounted within the recesses (17, 18) of the at least two tensioning blocks (11, 12).

20. In a device in accordance with claim 1, wherein a strap holder (70) is fastened on a side of the dental band (10) facing away from the tooth (50), and the strap holder (70) fastens one of a strap (30) and pieces of tubes (80).

* * * * *